United States Patent
Zanakis

Patent Number: 5,627,327
Date of Patent: May 6, 1997

[54] DYNAMIC SYSTEM FOR DETERMINING HUMAN PHYSICAL INSTABILITY

[76] Inventor: Michael Zanakis, 1 Ken Pl., Port Jefferson Station, N.Y. 11776

[21] Appl. No.: 685,951

[22] Filed: Jul. 22, 1996

[51] Int. Cl.$^6$ ................................................. A61B 5/00
[52] U.S. Cl. .................... 73/862.042; 73/865.4; 128/782
[58] Field of Search ....................... 128/779, 781, 128/782; 73/862.041, 862.042, 862.043, 862.044, 862.045, 862.046, 865.4; 273/449, 450; 364/463

[56] References Cited

U.S. PATENT DOCUMENTS

| | | | |
|---|---|---|---|
| 3,826,145 | 7/1974 | McFarland | 73/865.4 |
| 4,463,946 | 8/1984 | Wallace et al. | 273/449 |
| 5,186,062 | 2/1993 | Roost | 73/865.4 |
| 5,360,015 | 11/1994 | Heurte | 128/782 |

*Primary Examiner*—Richard Chilcot
*Assistant Examiner*—Ronald Biegel

[57] ABSTRACT

A dynamic system adapted to test a patient to determine the degree to which his physical stability is impaired and therefore predisposes the patient to injurious falls. The system includes a stable platform yielding signals that depend on the magnitude and direction of the force applied to the face of the platform. The platform is rendered unsteady by a convex rocker dish resting on the the platform face and having a flat top on which the patient stands. The resultant signals which are a function of the changing orientation of the flat top of the dish relative to the platform face are fed to a computer whose output is applied to a video monitor having a display screen on which is presented a cursor whose position is controlled by the signals. The standing patient, while viewing the screen, is required to so shift his weight on the rocker dish as to alter the orientation of the flat top to produce signals causing the cursor to travel from the center of the screen toward a computer-generated target presented on one corner of the screen, and to then acquire the target. The computer measures and scores the time it takes for the patient to cause the cursor to acquire the target as well as other variables that reflect the relative instability of the patient. These scores, taken together, define a stability index useful in deciding how then to treat the patient to improve his condition.

10 Claims, 1 Drawing Sheet

DYNAMIC SYSTEM FOR DETERMINING HUMAN PHYSICAL INSTABILITY

BACKGROUND OF INVENTION

1. Field of Invention:

This invention relates generally to apparatus adapted to determine the degree to which the physical stability of a patient is impaired, and more particularly to a dynamic system including a computer for this purpose which is responsive to shifts in the weight of a patient standing on an unsteady platform to provide measurements from which are derived a stability index useful in deciding how then to treat the patient so as to improve his condition.

2. Status of Prior Art:

The concern of this invention is with the physical balance or stability of a human subject and the degree to which balance is impaired and therefore requires corrective treatment appropriate to the subject's condition. Whether considered in mechanical terms or in the context of human physical behavior, stability is that property of a body which causes it to develop forces opposing any position or motion-disturbing influence. Stability therefore depends on being able to reach a state of equilibrium or balance.

An individual whose physical stability is impaired is then predisposed to falling down. The human body incorporates a complex balance-control mechanism, and any imbalance therein, regardless of its origin, leads to falling and this may have serious consequences.

The present invention resides in a dynamic system adapted to determine by means of an unsteady platform on which the subject being tested stands and a computer associated with the platform, the degree to which the stability of the subject is disturbed. The stability index yielded by the system makes it possible to then decide on the nature of the treatment appropriate to the subject's condition. (In the specification, the terms "subject" and "patient" are used interchangeably.)

The Kellogg International Work Group defines a fall as "an event which results in a person coming to rest inadvertently on the ground or other lower level, other than as a consequence of the following: sustaining a violent blow; loss of consciousness; sudden onset of paralysis, as in a stroke; or an epileptic seizure." A fall resulting from impaired stability lies within this definition, for the individual falls only because he is unable to maintain his balance.

As revealed by the available statistics, fatal falls in the United States often occur in elderly individuals, the mortality rate due to falls rising markedly with advancing age. Each year, a significant percentage of those individuals over 75 years of age who are brought to hospital emergency rooms are there because of a fall-related injury. And about 70% of general injury treatment in hospital emergency rooms in this age group is imputed to falling accidents.

Many senior individuals exhibit a proclivity for falling due to any number of neuromusculoskeletal dysfunctions. Brittle bones combined with slower reflexes result in bone breakage and other associated injuries and these are enormously expensive to repair. Several factors including age or sex are involved in identifying high-risk individuals, the probability of falling increasing exponentially with advancing age. Women appear to be at higher risk in most age groups.

Another risk factor is osteoporosis, which decreases bone resistance to mechanical injury, thereby increasing the risk of compression fractures. This then predisposes certain bones (hip, pelvis, forearm, vertebrae) to possible fracture. It is generally recognized that chronic diseases causing cardiovascular and neuromuscular dysfunction can significantly increase the risk of falling. Other factors also contribute to falls such, as gait and balance disturbances, poor vision, a disturbed mental state, and the use of medication or alcohol.

To prevent falls or to reduce their possibility, it is known to use screening techniques to identify high-risk individuals. Once a high-risk individual is identified, steps can then be taken to remove or minimize risk factors, such as by strengthening weak muscles or altering a drug regimen to avoid side effects resulting in a loss of balance. But an effective and reliable technique to screen such high-risk individuals has not heretofore been realized.

Thus numerous bio-mechanical techniques have been developed to analyze balance, but these have largely been static tests lacking components of dynamic response, or they were aimed at neuromuscular analysis and therefore not practical for screening. These and other previously known tests fail to take into account the matter of function; i.e., the physical abilities a subject actually needs in order to carry out daily activity. A static test, such as posturography, determines the amount of sway a subject exhibits when the subject is standing with his eyes open or closed. Such posturography tests have also evolved into a pseudo-functional test in which a subject stands on a static (non-moving) platform and shifts his weight in performing certain motor tasks while a computer monitors the results. Such motor tasks are similar to tracking a target, or using body sway to cause a video cursor to travel around a video "racetrack."

A known modification of pseudo-functional static testing is the incorporation therein of a bio-mechanical test using a force platform which pivots under the ankle and can slide front-to-back. This arrangement enables the researcher to induce sway and thereby determine the degree to which the subject can compensate by changing his posture.

These known testing techniques all suffer from a major flaw, for they are not really functional assessments. Since instability resulting in falls occurs during imbalance while walking (not standing still), in order to be effective a functional test must determine the ability of the subject to maintain balance during the performance of a task requiring body motion. Moreover, static or pseudo-functional balance testing is only effective for initial screening, in that patients gradually adopt a posture for control strategy after becoming familiar with the test conditions. Quantitative measures of adaptive abilities are therefore needed to make testing of equilibrium more useful clinically.

In equilibrium control, two information processes enable the subject to stand and walk over a variety of surfaces and conditions. There is redundant information supplied by sensory modalities related to orientation, these being somatosensory, vestibular and visual, all three having different frames of reference. There is also weighted information whereby the system modifies the relative importance of these inputs. However, under abnormal physiological conditions, such as when the subject suffers from a disease, either the inputs are disturbed or the weighted information may not be suitable for effective control of equilibrium.

As a consequence, compensation for the balance deficit may require another adaptive strategy. Indeed, it is the ability of a subject to modify balance strategy for proper equilibrium in response to various environmental challenges that makes quantitative assessments difficult. It is therefore necessary to utilize a system for equilibrium testing that incorporates a variety of support surface conditions that influence the vestibular system and the somatosensory input, yet simultaneously relies on a variety of visual conditions, all successively imposed on the subject being tested. A dynamic system in accordance with the invention does just that, and enables quantification of the subject's responses under such varied conditions.

Of prior art interest is the stability test disclosed in the article by Lord et al. "Exercise Effect on Dynamic Stability in Older Women" published in Arch Phys. Med. Rehabit. Vo. 77 March 1996 in which a subject being tested is coupled to a recording pen movable on an undulating track.

SUMMARY OF INVENTION

In view of the foregoing, the main object of this invention is to provide a dynamic system making use of an unsteady platform associated with a computer to determine the degree to which the physical stability of a patient standing on the platform is impaired.

A significant feature of a system in accordance with the invention is that the patient performs a task on an unsteady platform and as the platform shifts, the patient's adaptive abilities must change rapidly to accommodate the shifting platform and the performance of the task.

Also an object of this invention is to provide a system of the above type in which a computer analyzing the performance of a patient standing on an unsteady platform produces an accurate reading of the patient's performance regardless of the physiological or psychological conditions responsible for the patient's impaired stability.

A salient advantage of a dynamic system in accordance with the invention is that it is capable of determining the balance and equilibrium functions of the subject being tested. A comprehensive functional test is performed by taking into account the various changes in posture required to maintain equilibrium under various visual, sensory or vestibular stimuli. This functional equilibrium and balance test makes it possible to predict the likelihood of a serious fall in elderly individuals or other patients.

Though there are many motion analysis facilities throughout the United States, these are mainly focused on a single diagnosis related to a specific disease such as parkinson's disease or cerebral palsy. A system in accordance with the invention provides an integrated assessment using a biomechanical device and computer software that yield rapid and reproducible results.

A computer-assisted motion analysis system in accordance with the invention reliably measures bio-mechanical functions under controlled physical conditions, the system assessing components of movement such as motor reaction time, movement time, velocity and postural stability. The test uses a computer-generated video task performance program requiring the patient to track a video target with a cursor projected onto a video screen. The cursor is guided in real time by the patient moving his body on an unsteady platfrom which senses changes in the patient's center of gravity.

The results derived from the patient's motion in the course of specific tests are calculated and scores are obtained, which assign the patient to a low, medium-or high instability category. The resultant stability profile can be used to predict the likelihood of a fall. Ultimately, the scores serve as a guide to appropriate preventive measures such as physical therapy (muscle strengthening), exercise, environmental changes (e.g., installing home handrails), orthotics and drug therapy. These preventive measures greatly reduce the probability that a severe fall will occur.

Briefly stated, these objects are accomplished by a dynamic system adapted to test a patient to determine the degree to which his physical stability is impaired. The system includes a stable platform yielding signals that depend on the magnitude and direction of the force applied to the platform face. The platform is rendered unsteady by a convex rocker dish resting on the face of the platform and having a flat top on which the patient stands. The resultant signals which are a function of the orientation of the flat top of the dish relative to the platform face are fed to a computer whose output is applied to a video monitor having a display screen on which is presented a cursor which position is controlled by the signals.

The standing patient, while viewing the screen, is required to so shift his weight on the rocker dish as to alter the orientation of the flat top to produce signals causing the cursor to travel from the center of the screen toward a computer-generated target presented on one corner of the screen and to then acquire the target. The computer measures and scores the time it takes for the patient to cause the cursor to acquire the target as well as other variables that reflect the relative stability of the patient. These scores, taken together, define a stability index useful in deciding how then to treat the patient to improve his condition.

BRIEF DESCRIPTION OF DRAWINGS

For a better understanding of the invention, as well as other objects and features thereof, reference is made to the accompanying of drawings wherein.

DETAILED DESCRIPTION OF INVENTION

Figure 1:
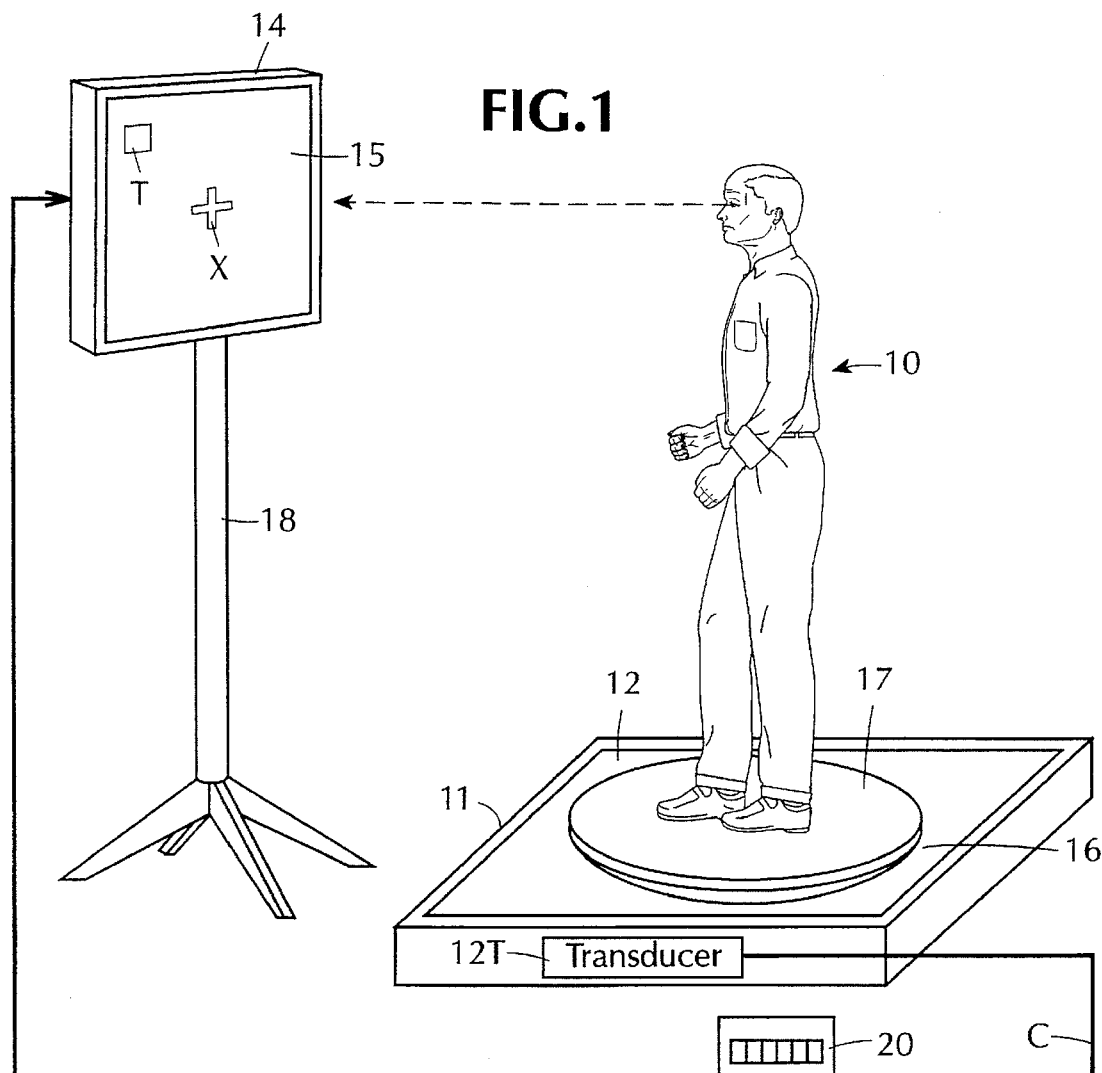
FIG. 1 schematically illustrates a dynamic system in accordance with the invention in which a patient to be tested stands on an unsteady platform.

The Dynamic System:

Referring now to FIG. 1 of the drawing, shown in this figure is a dynamic system in accordance with the invention which functions to determine the degree to which a human subject (patient 10) suffers from an impaired physical stability and is therefore predisposed to injurious falls. The cause or source of such instability is not the concern of the system, but only the degree of its existense. Obviously a patient whose physical stability is only slightly impaired has a much lower predisposition to falling down than one having a much greater degree of impairment. An accurate determination of the degree of impairment is therefore a useful guide to a physician or therapist prescribing a proper treatment to improve the patient's condition.

The system includes a stable force platform 11 placed on the floor of the test facility. Platform 11 is provided with a horizontal face 12 below which is a transducer 12T responsive to a force applied to the face to generate analog electrical signals that are a function of the magnitude and direction of the force along three axes of movement (the X, Y and Z coordinates). Transducer 12T may be formed of piezoeletric, magnetostrictive, capacitative or other elements responsive to the direction and magnitude of an applied pressure or force.

The signals yielded by transducer 12T are fed via a cable C to the data acquisition board of a digital computer 13 which processes the data, the output of which is applied to a video monitor 14 having a large, generally rectangular video display screen 15. A preferred computer for this purpose is a IBM386 or a similar unit that includes a high-speed data acquisition board for an analog-to-digital input. The IBM unit is capable of handling 6 channels of input at approximate 100 MHz.

Resting on the horizontal face 12 of platform 11 and serving to render the platform effectively unsteady is a rocker platform 16 in the form of a shallow large-diameter convex dish having a flat top 17. When a test is to be conducted, patient 10 must then stand on flat top 17 while viewing screen 15 of the video monitor. Video monitor is mounted on a stand 18 of adjustable height. The monitor is placed about six feet away from the standing patient and its adjusted height is such as to bring screen 15 in line with the level of the eyes of the patient who can then view the screen without difficulty.

In an actual working embodiment, rocker dish 16 which is farmed of steel and is therefore heavy, has a 30 inch diameter and an 8 foot radius of curvature. Hence the rockability of the dish is limited and the patient standing on the flat top of the dish remains at an erect position as he rocks the dish in a manner to be later explained.

The bottom center of the convex dish 16 rests on the center of face 12 of platform 11. The feet of patient 10 are placed within the central region of the flat top 17 of the dish, this region being marked to indicate where the patient is to stand. To properly stand on the flat top 17 of the dish whose center is at the intersection of horizontal and vertical diametrical lines, the feet of the patient should lie on the horizontal line on either side of the center and equally spaced from the center, the feet being separated a shoulder-width apart. This symmetrical stance on the rocker dish is the ideal stance, but it is not necessary to assure this stance to obtain reasonably accurate readings.

Stable platform 11, in the absence of rocker dish 16, provides a static test. But when rocker dish 16 rests on the platform, it then renders standing surface 17 unsteady and thereby adds a dynamic or functional test component thereto. A patient standing on the rocker dish has to exert fine neuromuscular control of his posture to maintain his balance while undergoing a test.

Figure 2:
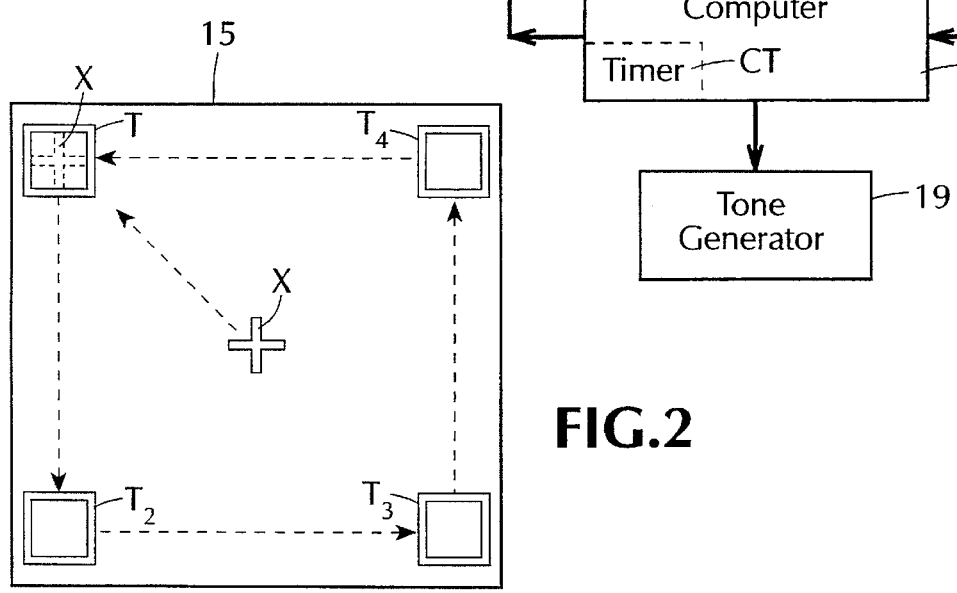
FIG. 2 shows the screen of the video monitor included in the system.

Generated in computer 13 and presented on screen 15 of video monitor 14 is a cursor X having a cruciform or cross-like formation, very much like the familiar Red Cross symbol. As best seen in FIG. 2, cursor X which is formed by a vertical bar intersected at its midpoint by a horizontal bar of the same length, is initially at the center of video screen 15. In an actual embodiment, the dimensions of the cursor X are such that the cross fits within a three-inch imaginary square and has a bar thickness of ⅛ inch. Hence cursor X is clearly visible to patient 10 standing six feet away from the screen.

Also presented on screen 15 is a computer-generated target T formed by a square box whose dimensions correspond to that of the imaginary square into which cursor X fits, the square box of the target being framed by a square border. Thus target T has a 3 inch square box and a border whose four sides have a ⅛ inch thickness. When the center point of the cross of cursor X lies within the box of target T, it is then said to have acquired the target. But if the center point of the cursor cross lies in the border of the target or is outside the border, the cursor does not then acquire the target.

Target T is initially presented on video screen 15 adjacent to its upper left corner, as best seen in FIG. 2. Target T is made distinguishable from cursor X by giving it a different color, hue or brightness. The test to which patient 10 is subjected, requires him to move the signal-controlled cursor X toward target T so that it acquires the target. In order to move the cursor, the patient must so rock the unsteady dish on which he is standing as to produce platform signals causing the cursor to move in the desired direction.

Test Procedure:

When patient 10 to be tested stands still with his feet on the central region of the flat top 17 of convex dish 16, the flat top is then oriented so as to lie in parallel relation to the horizontal face 12 of platform 11. In this initial state, the signals then yielded by platform transducer 12T cause cursor X responsive to these signals to occupy the center position of video screen 15 as shown in FIG. 2.

In the course of a test, patient 10 standing on rocker dish 16 and observing cursor X on video screen 15 is required to shift his weight on the rocker dish and therefore his center of gravity so that the resultant signals yielded by transducer 12T cause cursor X to travel from its initial center position on the screen in a direction and to an extent determined by the manner in which the patient shifts his weight and in doing so modulates these signals.

By shifting his weight forward and to the left, the flat top 17 of the rocker dish is then oriented relative to the platform face 12 to produce signals causing cursor X to travel from the center of the screen toward target T and to acquire the target which in the first phase of the test procedure is located adjacent to the upper left corner of video screen 15.

Computer 13 is provided with a tone generator 19 which produces an audible tone which acts as a cue for the patient hearing this tone. As long as cursor X is visibly within target T, the audible tone has a high-frequency, such as 800 Hz. Should cursor X move out of the target, so that the center of the cursor cross is outside of the square box of the target, audible tone remains "on" but then has a lower frequency, such as 500 Hz. Hence the frequency of the tone tells the patient whether or not target T has been acquired by the cursor X.

Included in computer 13 is an internal timer CT, the computer being programmed to cause the timer to start a count of 5 seconds when cursor X moves away from its center position on the screen as a result of a rocking motion imparted to dish 16 by patient 10 standing on its flat top and acquires the target. During this 5 seconds timed interval, the patient must try as best he can to keep cursor X within target T.

At the conclusion of the 5 seconds timed interval in the first phase of the test procedure during which target T is positioned adjacent the upper left corner of video screen 15, computer 13 then instantly shifts the target to a position adjacent the bottom left corner of the screen, as indicated by target $T_2$ in FIG. 2. During this change in target position, the position of cursor X remains unchanged.

When patient 10 is presented with target $T_2$ at the bottom left corner of the video screen 15, this begins the second phase of the test procedure. In this second phase, patient 10 must now seek to have cursor X acquire target $T_2$. To do so patient 10 must now shift his weight on rocker dish 16 to the rear and left in order to produce platform signals causing cursor X to move toward and acquire target $T_2$. And the patient must do his best to keep cursor X within target $T_2$ during the timed 5 seconds interval in the second phase of the test procedure.

At the conclusion of this 5 seconds interval, computer 13 then brings about another shift of the target position to present a target $T_3$ at the bottom right corner of screen 15 as shown in FIG. 2, this being the third phase of the test procedure.

Now the patient must shift his weight on the rocker dish to repeat the process to cause cursor X to move toward and acquire target $T_3$. At the conclusion of the third phase, the computer moves the target to the upper right corner of the screen to present a target $T_4$. The patient must again shift his weight to repeat the process in the fourth phase of the test procedure. Finally the target again shifts to the top left corner of the screen, and this too must be acquired.

The patient actually is given as much time as he wants to go from target to target. However, once a target is acquired, the 5 second timer CT proceeds to time and the patient has only five seconds to keep the cursor stable; that is within the box of the target.

Five seconds is allowed once a target is acquired whether or not the patient in any one phase of the test procedure is unable to keep cursor X within the confines of the target then being presented on the screen regardless of how many times during this period the border of the target is traversed by the cursor. Computer 13 "times out" after 60 seconds if a target cannot be acquired at all and acts to shift the target to the next corner of the screen.

Measurements:

Computer 13 is programmed by appropriate software to carry out measurements of the following values, each one of which represents a variable that depends on the relative stability of the patient tested.

Value A "Reaction Time" (RT):

Variable RT represents time in seconds it takes for a patient, when first presented with a target at one corner of the screen, to then cause the cursor X to begin moving toward the target. In a physiological sense, this variable represents the time elapsed between cognition and the initiation of motor activity.

Value B "Movement Time" (MT):

Variable MT represents the time it takes in seconds for the patient to cause cursor X to move toward and be acquired by the target. This variable therefore represents the time of acquisition from target to target.

Value C "Average Velocity" (V):

Variable V which is expressed in inches per second, is calculated as the total distance travelled by the cursor once acquired by the target, divided by five seconds. This variable reflects oscillation of the cursor with respect to the target as a result of unsteadiness on the part of the patient. Hence it provides an indication of the patient's ability to maintain steadiness.

Value D "Stability" (S):

Variable S represents the cumulative time in seconds within the target zone divided by the total number of times the cursor moves beyond the border of the target. This variable is therefore indicative of the patient's ability to provide sufficient neuromuscular control to maintain the cursor within the target.

The objective of the test procedure is to determine the degree of stability patient 10 is capable of attaining under normal conditions, not under conditions in which the patient is functioning poorly. Hence the patient is urged by the operator of the system to acquire the target as rapidly as it is possible for him to do so, and the patient is encouraged in the course of the test procedure to do the best he can in order to get the highest possible score. The best score the patient can attain affords the most accurate reading of the actual degree to which the patient's stability is impaired.

To this end, the five-phase test procedure is carried out three times, the first two being trial runs whose scores are examined and then discarded. The values achieved in the third and final run are the only ones used and averaged, for these are the most reliable indications of the patient's degree of instability.

The scores produced by the third run taken together, afford a qualitative dynamic profile of the physical characteristic associated with volitional movement of the patient during a "functional" test. This profile represents a stability index and is predictive of the probability of a fall.

A slow reaction time RT is indicative of a patient having poor neuromuscular control. A patient having a slow reaction time cannot reflexively adapt to the changing environment with adequate postural adjustments. A slow movement time MT generally indicates a bradykinesia, or slowness of movement. This is often found in parkinsonism, and is also a major factor in inadequate postural control.

A velocity (V) score of 5 indicates cross of the cursor over and into the target box only, with no subsequent movement over the target's border to the outside of the box. A velocity (V) score of 1 indicates that the subject moved the cursor over the target borders 5 times (regardless of the direction of movement). It therefore indicates that the subject is less stable than a subject who scores a 5. The higher this score, the more stable the balance and compensatory mechanism.

A velocity (V) of approximately 3 inches per second (ips) and a stability S of approximately 5 indicates that the subject rapidly and effectively acquires the target and remained in the target zone. A higher velocity is usually associated with unsteadiness, and therefore a lower stability score, since the subject tends to oscillate the cursor rapidly about the target zone. Conversely, a slower velocity V and a better stability S means that while the subject can maintain steadiness within the target zone, the postural responses needed are slow and not as effective. Slow velocity V and poor stability S indicates compounded difficulties in neuromuscular control. The scores of values A, B, C and D yielded by computer 13 are printed out on a printer 20 associated with the computer, the printout providing a stability index indicative of the degree to which the patient's stability is impaired.

Usefulness of Results:

The system in accordance with the invention acts to measure quantitatively specific components of movement, the computer assessing various movement parameters associated with balance. In practice, the stability index data derived from one patient can be compared to those derived from other patients in a data base, including normal young individuals who were subjected to the same test procedures. By means of software, one can correlate the test results and assign stability scores to each patient to determine his degree of instability and the concomitant probability of falling.

All patients should first be screened to grossly determine. their motor performance using subjective assessments, as well as a history and a physical. For example, determining that the patient requires mechanical support (cane, walker, etc.) would place the patient in a high risk fall category. However, in patients without overt signs of instability, the system will provide an objective and quantifiable assessment of their instability (i.e., a fall index).

A physician can use this index as the rationale for prescribing specific treatments. Such treatments can range from referral to specialists (for example, in orthopedic surgery) to consultation or referral to a physical therapist, who can then prescribe, for example, orthotics or exercise. In this way the physician can more reliably insure that the patient will be able to avoid a debilitating fall.

Since the system acts to assess stability, other uses of stability analysis aside from fall prediction are then possible. Motor dysfunctions associated with disease states such as parkinson's disease can be quantified to determine the effectiveness of a drug regimen on that disease, or even the progression of the disease (i.e., its progressive motor deterioration).

Also, various states of muscle weakness can be quantified, for prescribing and targeting proper muscle strengthening therapies. This is important from the perspective of rehabilitation of injured limbs and post-operative procedures whereby recovery can be monitored to effeciently correlate length of hospital stay or the amount of rehabilitation required. Care of the elderly with regard to stability testing for fall prediction and management can also be extended to treatment of musculoskeletal dysfunction, and care as well as for muscle strengthening to alleviate a weakness. Finally, from a sports medicine perspective, the system is useful, for it can provide information regarding motion and balance during certain physical activities whereby the activity can be modified to alter performance.

While there has been shown a preferred embodiment of a dynamic system in accordance with the invention, it is to be understood that many changes may be made therein without departing from the spirit of the invention.

I claim:

1. A dynamic system adapted to test a human subject to determine the degree to which his physical stability is impaired without regard to the cause of impairment, the system comprising:

A. a stable platform having a horizontal face below which is a transducer yielding signals which are a function of the magnitude and direction of a force applied to the face; and B. a rocker platform formed by a convex dish which rests on the face of the stable platform and is provided with a flat top on which the subject to be tested stands, the flat top being normally parallel to the face, whereby when the standing subject shifts his weight on the dish to change the orientation of the flat top relative to the face, the resultant signals are indicative of the degree to which the stability of the subject is impaired.

2. A system as set forth in claim 1, in which the transducer is formed of piezoelectric elements.

3. A system as set forth in claim 1 in which the rocker platform is formed of metal and has a diameter exceeding two feet.

4. A system as set forth in claim 1, further including a computer whose output is applied to a video monitor having a screen on which are presented a computer-generated cursor and a target which appears at a corner of the screen, the transducer signals being fed into the computer to control the position of the cursor whereby the subject standing on the dish and viewing the screen, by shifting his weight can cause the cursor to move toward and acquire the target.

5. A system as set forth in claim 4, in which the cursor has the form of a cross created by intersecting horizontal and vertical bars that fit within an imaginary square.

6. A system as set forth in claim 5, in which the target is formed by a square box which matches said imaginary square and is framed by a square border, the cursor acquiring said target when its point of intersection lies within the box.

7. A system as set forth in claim 6, in which the computer is provided with a tone generator which produces a tone of one frequency when the target is acquired by the cursor and a tone of another frequency when the point of intersection is outside the box of the target.

8. A system as set forth in claim 4, in which the computer includes means to measure the time it takes for the cursor to move from a center position on the screen to a position at which it acquires the target.

9. A system as set forth in claim 4, in which the computer includes means to measure the time it takes for the subject to react to the target when it is first presented on the screen to cause the cursor to move toward the target.

10. A system as set forth in claim 4, in which the computer includes means to measure the total distance travelled by the cursor once it acquires the target divided by a predetermined number of seconds.

* * * * *